United States Patent
Delforge

(10) Patent No.: US 9,912,254 B2
(45) Date of Patent: Mar. 6, 2018

(54) NON-CONTACT ROTARY POWER TRANSFER SYSTEM

(71) Applicant: Analogic Corporation, Peabody, MA (US)

(72) Inventor: Adrian Delforge, Rockport, MA (US)

(73) Assignee: Analogic Corporation, Peabody, MA (US)

( * ) Notice: Subject to any disclaimer, the term of this patent is extended or adjusted under 35 U.S.C. 154(b) by 341 days.

(21) Appl. No.: 14/041,497

(22) Filed: Sep. 30, 2013

(65) Prior Publication Data

US 2014/0098929 A1 Apr. 10, 2014

Related U.S. Application Data

(63) Continuation of application No. 12/517,329, filed as application No. PCT/US2007/088117 on Dec. 19, 2007, now Pat. No. 8,581,437.

(60) Provisional application No. 60/876,055, filed on Dec. 20, 2006.

(51) Int. Cl.

| | |
|---|---|
| H05G 1/10 | (2006.01) |
| H02M 7/5387 | (2007.01) |
| A61B 6/00 | (2006.01) |
| H01F 38/18 | (2006.01) |
| H02J 5/00 | (2016.01) |
| A61B 6/03 | (2006.01) |
| H01F 38/14 | (2006.01) |

(52) U.S. Cl.
CPC ......... *H02M 7/53871* (2013.01); *A61B 6/035* (2013.01); *A61B 6/56* (2013.01); *H01F 38/18* (2013.01); *H02J 5/005* (2013.01); *H05G 1/10* (2013.01); *H01F 2038/143* (2013.01); *H01F 2038/146* (2013.01); *Y10T 307/25* (2015.04)

(58) Field of Classification Search
CPC ....................................................... H05G 1/10
USPC .................................................. 307/17, 153
See application file for complete search history.

(56) References Cited

U.S. PATENT DOCUMENTS

| | | | | |
|---|---|---|---|---|
| 4,654,770 A | * | 3/1987 | Santurtun | H05G 1/54 361/93.9 |
| 4,797,908 A | * | 1/1989 | Tanaka | H05G 1/20 363/28 |
| 4,912,735 A | * | 3/1990 | Beer | A61B 6/035 378/15 |

(Continued)

*Primary Examiner* — Adi Amrany
(74) *Attorney, Agent, or Firm* — Cooper Legal Group, LLC

(57) ABSTRACT

A power delivery system includes a rotary transformer having a primary winding and a secondary winding and configured to transfer power between stationary coupling elements on a stationary side and rotational coupling elements on a rotational side. The rotational coupling elements share a central axis with the stationary coupling elements, and are adapted to rotate with respect to the stationary coupling elements. The power delivery system includes an isolation transformer that drives the primary winding of the rotary transformer, and a plurality of power inverter stages whose outputs are adapted to be summed and coupled to the rotary transformer. A plurality of output power converters receive transmitted power from the rotary transformer. A plurality of control elements, disposed on the rotating side, are configured to close a feedback loop on desired and actual performance of the output power converters, and to control the power inverter stages.

20 Claims, 11 Drawing Sheets

(56) References Cited

U.S. PATENT DOCUMENTS

| | | | | |
|---|---|---|---|---|
| 5,272,618 A * | 12/1993 | Blake | H02M 3/3378 | 363/25 |
| 5,339,348 A * | 8/1994 | Wirth | H05G 1/20 | 378/91 |
| 5,608,771 A * | 3/1997 | Steigerwald | A61B 6/56 | 378/15 |
| 5,646,835 A * | 7/1997 | Katcha | H02M 3/337 | 324/322 |
| 6,012,736 A * | 1/2000 | Hansen | B60R 21/01 | 280/731 |
| 6,441,511 B1 * | 8/2002 | Masudaya | B60R 16/027 | 180/274 |
| 6,800,957 B2 * | 10/2004 | Nerone | H02J 1/08 | 307/9.1 |
| 7,054,411 B2 * | 5/2006 | Katcha | H05G 1/10 | 336/105 |
| 7,375,993 B2 * | 5/2008 | Beland | H02M 1/088 | 363/132 |
| 7,613,273 B2 * | 11/2009 | Beyerlein | A61B 6/56 | 361/143 |
| 7,848,482 B2 * | 12/2010 | Nakayama | A61B 6/035 | 378/101 |
| 7,899,150 B2 * | 3/2011 | Beyerlein | A61B 6/56 | 378/101 |
| 7,957,786 B2 * | 6/2011 | Katcha | A61B 6/56 | 336/145 |
| 8,571,179 B2 * | 10/2013 | Beland | H05G 1/32 | 378/101 |
| 2006/0284568 A1 * | 12/2006 | Chang | H05B 41/2827 | 315/282 |
| 2007/0035883 A1 * | 2/2007 | Katcha | A61B 6/56 | 360/281.8 |
| 2007/0279002 A1 * | 12/2007 | Partovi | H02J 7/0027 | 320/115 |
| 2008/0095314 A1 * | 4/2008 | Katcha | A61B 6/032 | 378/101 |
| 2009/0116618 A1 * | 5/2009 | Nakayama | A61B 6/035 | 378/107 |

* cited by examiner

NON-CONTACT ROTARY POWER TRANSFER SYSTEM

CROSS REFERENCE TO RELATED APPLICATIONS

This application is a continuation of U.S. patent application Ser. No. 12/517,329, filed on Nov. 23, 2009 and entitled "Non-Contact Rotary Power Transfer System," which is a national phase entry of PCT Application No. PCT/US07/88117, filed on Dec. 19, 2007 and entitled "Non-Contact Rotary Power Transfer System" and claims the benefit of U.S. Provisional Application No. 60/876,055, filed on Dec. 20, 2006 and entitled "Isolated Modular, Multichannel And Multiphase Contactless Rotary Power Transfer System." The U.S. Patent Application, PCT Application, and Provisional Application are incorporated herein by reference.

BACKGROUND

The next generation of medical computed tomography (CT) equipment may have to address increasing demands for operational modalities and reduced patient dose. Modalities such as real-time cardiac imaging may require faster rotational speeds, and high voltage responses with higher peak powers. Increased power may require more disc space for increased tube cooling and more space for the traditional high voltage power supply. It is desirable to provide solutions to these challenges that do not place excessive constraints on a CT design. The need for reliable performance at higher rotational speed and power may require a new approach to rotational high voltage power generation.

SUMMARY

A power delivery system may include a rotary transformer having a primary winding and a secondary winding. The rotary transformer is configured to transfer power between one or more stationary coupling elements disposed on a stationary side of the rotary transformer, and one or more rotational coupling elements disposed on a rotating side of the rotary transformer. The rotational coupling elements share a central axis with the stationary coupling elements, and are adapted to rotate with respect to the stationary coupling elements.

The power delivery system may further include an isolation transformer adapted to drive the primary winding of the rotary transformer, and a plurality of power inverter stages. The plurality of power inverter stages are configured to provide input power to the primary winding of the rotary transformer. The outputs of the power inverter stages are adapted to be summed and coupled to the isolation transformer.

The power delivery system may further include a plurality of output power converters that are configured to receive transmitted power from the rotary transformer, and to convert the received power to a desired range for the rotational coupling elements.

The power delivery system further includes a plurality of control elements disposed on the rotating side of the rotary transformer. The plurality of control elements are configured to close a feedback loop on desired and actual performance of the plurality of output power converters, and to provide to the stationary side of the rotary transformer one or more timing signals to control the power inverter stages.

DETAILED DESCRIPTION

Systems and methods are described that deliver power to a rotating system without physical contacts (such as brushes) and at high speeds (for example greater than about 300 RPM), while increasing the available space on the rotating gantry by relocating the large power inverter of the high voltage and auxiliary power supplies to the stationary frame. In particular, a rotary transformer that couples power between a stationary side and a rotating side is described. Isolation and decoupling of the main power supply is achieved through an isolation and summing transformer that drives the primary winding of the rotary transformer in a multi phase configuration. Applications that may use the non-contact power delivery system described in the present disclosure include, but are not limited to, CT (computed tomography) systems.

Figure 1:
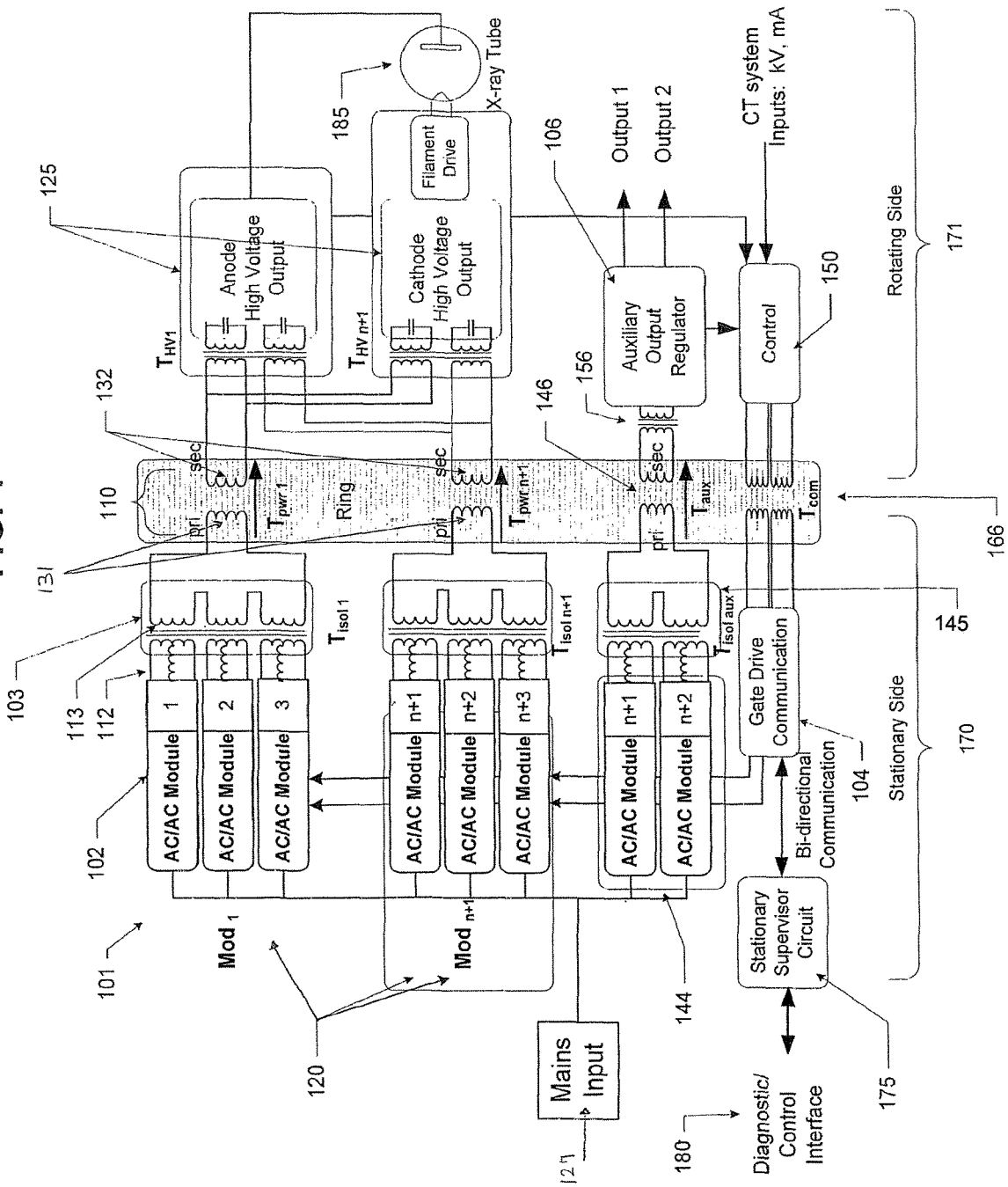
FIG. 1 illustrates a non-contact power transfer system in accordance with one embodiment of the present disclosure.
Figure 11:
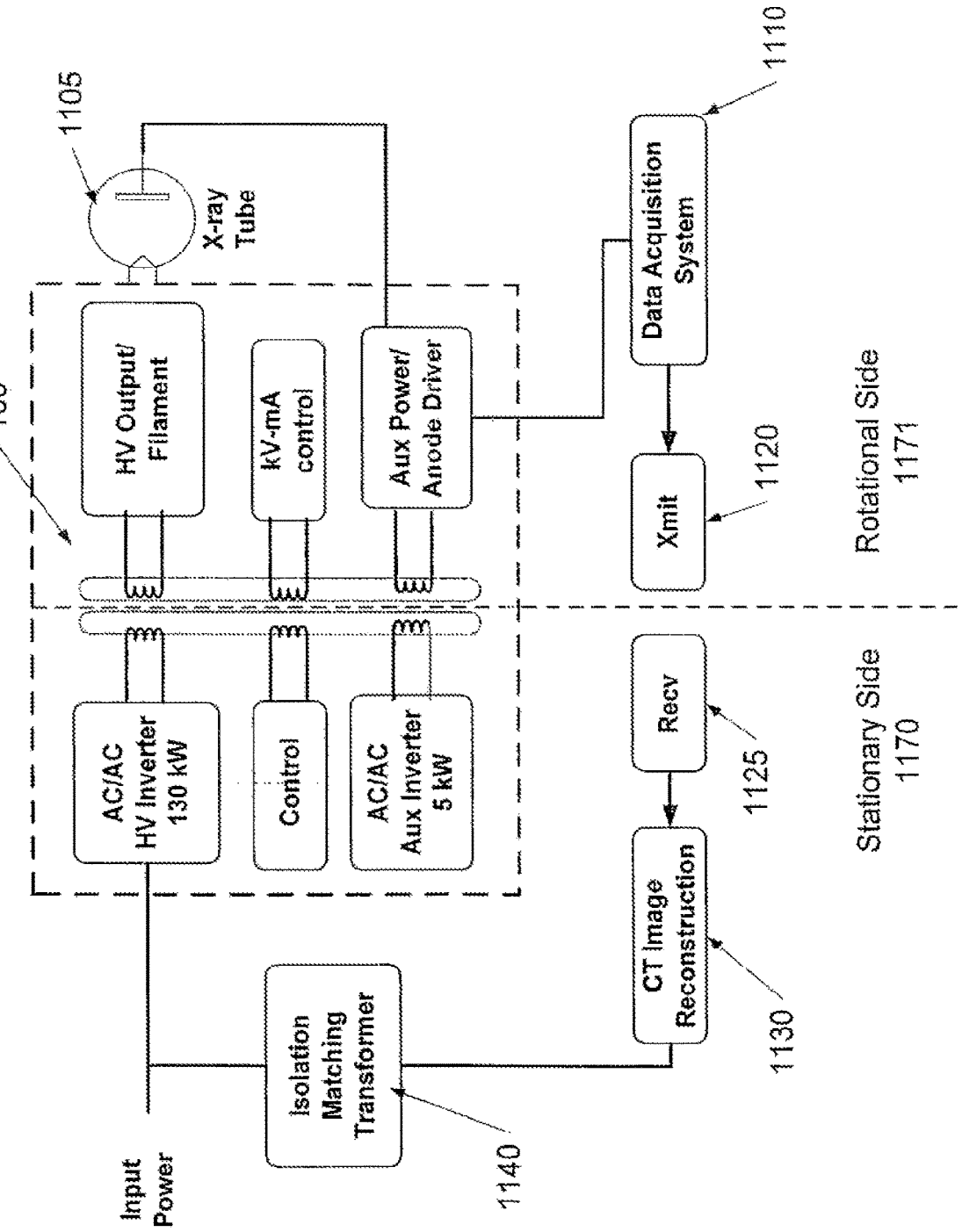
FIG. 11 is a system level diagram of a CT system that utilizes the non-contact power transfer system illustrated in FIGS. 1 and 10.

FIG. 1 illustrates a non-contact power transfer system 100 in accordance with one embodiment of the present disclosure. While the embodiment illustrated in FIG. 1 may be used in CT scanners as illustrated in FIG. 11, in different embodiments of the present disclosure the system 100 may be used in applications other than CT, and in particular in any application that requires transfer of induced power between one or more stationary elements and one or more rotational elements.

In particular, the system 100 illustrated in FIG. 1 includes: a split (or gapped) rotary transformer 110; a set 101 of modular power inverter stages 102; a balanced and shielded isolation/summing transformer 103; and an auxiliary transformer 146 whose output is regulated by an auxiliary output regulator 106. A gapped rotary transformer is also commonly referred to as a ring. In this patent, the terms "rotary transformer" and "ring" have the same meaning, and are used interchangeably. In the embodiment illustrated in FIG. 1, the power delivery system 100 is configured to deliver power to an x-ray tube 185. In other embodiments, the power delivery system discussed in the present disclosure may be configured to deliver power to devices other than an x-ray tube.

The rotary transformer 110 transfers power between one or more stationary coupling elements located on a stationary side 170 of the rotary transformer, and one or more rotational coupling elements located on a rotational side 171 of the rotary transformer 110. The rotational coupling elements are adapted to rotate with respect to the stationary coupling elements, and share a common axis with the stationary coupling elements. The rotary transformer 110 has a primary winding(s) 131 and a secondary winding(s) 132, and transfers induced power to a high voltage output module(s) 125 connected to the secondary winding(s) 132.

The design shown in FIG. 1 utilizes a high frequency, high power inverter system 120 that includes the above-mentioned set 101 of lower power inverters 102. Power is supplied through a mains input 127, which is the power source from the electric power facility. The isolation transformer 103 has a primary winding(s) 112 and a secondary winding(s) 113. The outputs of the inverters 102 are adapted to be summed at the primary winding 112 of the isolation and summation transformer 103. The secondary winding 113 of the isolation transformer 103 drives the primary 131 of the gapped rotary transformer 110 that transfers induced power to the high voltage output module 125.

The set 101 of modular power inverters 102 are located on the stationary side 170 of the rotary power transformer 110. The multiple AC/AC high frequency inverter modules 102 may each include an integrated mains input rectifier, boost pre-regulator and full bridge inverter configured in a non-series resonant topology. The pre-regulator may be configured as a boost stage so as to provide wide compliance for nominal 380-480 main power supplies that optimizes post inverter efficiency, as illustrated and described in more detail in conjunction with FIG. 4.

The balanced and shielded isolation/summing transformer 103 sums the full bridge inverter outputs 112, and isolates the outputs 112 from the primary winding 131 of the rotary transformer 110. The isolation and summing transformer 103 provides double isolation from the main power supplies 101 to the primary winding 131 of the rotary transformer 110.

In the illustrated embodiment, the isolation transformer 103 is a double insulation (DI) element that acts as a balanced, shielded, high frequency safety isolation transformer. The isolation transformer 103 substantially reduces leakage currents that are normally induced into the housing of the rotary transformer 110 via multiple capacitive shields. The isolation transformer 103 also provides a center point that eliminates imbalanced common mode voltages driving the primary winding 131 of the rotary transformer 110. Housed within the inverter, the isolation transformer 103 provides for a low noise, non-earth based drive signal to the primary winding 131 of the rotary transformer 110. The isolation transformer 103 also provides the full voltage isolation required by safety regulations without requiring the rotary transformer's primary to secondary windings to provide anything more than functional insulation. In this way, the need for a PE ground connection capable of handling high fault currents to the rotational coupling elements is eliminated.

The main power source is derived from multiple inverters 102, each operating in a plurality of modes. In one embodiment, variable frequency may be employed to maintain a wide range of power delivery in a resonant configuration by moving the operating frequency away from the resonant frequency. Phase shifting at high frequencies substantially extends the output regulation, down to virtually 0% of output power. The selective disengagement of multiple inverters may also be employed for increased efficiency at low power levels. The above-described approach allows for efficient power conversion and power regulation, by reducing the switching losses at high power conditions and allowing for minimal circulating currents in the resonant circuit for low power modes. The topology of the power transfer system 100 further provides complete output power control using a phase shift technique of the inverter bridge to the primary 112 of the isolation transformer 103. This phase shift technique reduces high circulating current in the secondary of the rotary transformer 110, which further improves efficiency.

In the illustrated embodiment, multiple inverters can be selected on the fly to add or subtract power delivery at the isolation and summing transformer 103, to manage a dynamic load resulting from a fast time varying emission current requirement imposed by new image and dose management protocols while maximizing efficiencies. Variations in the operating frequency of the inverter system relative to the resonant frequency in the high voltage LC circuit provide an impedance mismatch altering the power delivery. A dynamic range of about 1:20 may be achieved over a range of operating frequencies while phase shifting of multiphase inverters provides for an output substantially near 0%.

Auxiliary Power

Auxiliary power may be provided by inverters that are located on the stationary side 170 of the rotary transformer 110 and that operate at a fixed frequency and duty cycle. In the embodiment illustrated in FIG. 1, auxiliary power is provided through an additional inverter 144 that is also isolated, via an auxiliary isolation transformer 145, from an auxiliary winding 146 and separate multi output transformer 156, which operates continuously with load regulation from the auxiliary output regulator 106 for multiple voltage outputs on the rotating side 171 managed directly by a control element 105 located on the rotating side.

As shown in FIG. 1, a bi-directional low speed supervisory communication path is incorporated into a gate drive control winding 166 by modulating the data with a high frequency carrier. Regulation of the various outputs is performed on the rotating side 171, eliminating the feedback requirement to the stationary side 170 and providing for fast response to load variations. A multi-tapped transformer winding 156 connected to the secondary of the auxiliary winding 146 of the rotary transformer 110 provides for various output voltages each with their own regulating circuit on the rotating side 171. This technique provides for isolation between the main auxiliary power supplied to the cooling system and tube drive circuitry from that of the sensitive data collection circuits. An alternative construction of a multi tapped secondary ring winding provides equivalent function at reduce space.

Feedback and Control

In the embodiment illustrated in FIG. 1, the feedback and control of the main stationary side inverters 102 are managed on the rotation side 171 and only simple timing signals are provided to the stationary based inverters 102 through a coupled control winding. In this way, the ultra-high speed, non-contact digitized, transmission systems to control the stationary elements are eliminated. In particular, all control of the delivered power (not limited to high voltage) is performed via one or more control elements 150 located on the rotating side. The high fidelity feedback required for fast rate of rise on the high voltage output is maintained by analog circuitry on the rotating side without digitization, coding, and transmission thereby eliminating the need for a high bandwidth data link. As seen in FIG. 1, the control element(s) 150 may receive input information from a CT system, in embodiments in which the power transfer system 100 is used for the CT system.

The one or more control elements 150, disposed on the rotating side of the rotary transformer, are configured to close a feedback loop on desired and actual performance of the output power converters, and provide to the stationary side of the rotary transformer one or more timing signals to control the power inverter stages.

The control element 150 may comprise a control loop circuit configured to close a feedback loop on desired and actual performance of output power converters that receive transmitted power from the rotary transformer and convert the received power to a desired range for the rotational coupling elements. The control loop circuit, which determines the required sub μsec timing of phase and pulse width of the inverters' gate drive control signals, is maintained and presented via timing signals in an analog representation. These timing signals are transmitted to the stationary side 170. As the timing signals are analog, they maintain the real time information while requiring no further processing and can immediately be applied to the power inverter gate drive circuitry 104 in the original form without latency or delay.

The windings of the rotary transformer are further adapted for dual use that allows for bi-directional communication through superposition of one or more coupled high-frequency modulated signals. The dual use may include a first use in which power signals or timing signals are transmitted through the windings, and a second use that provides for bi-directional communication. In the embodiment illustrated in FIG. 1, the bi-directional communication may be between the gate drive circuitry 104 and a stationary supervisor circuit 175. The stationary supervisor circuit 175, in turn, may be connected to a diagnostic/control interface 180.

Isolation/Shielding

Figure 2:
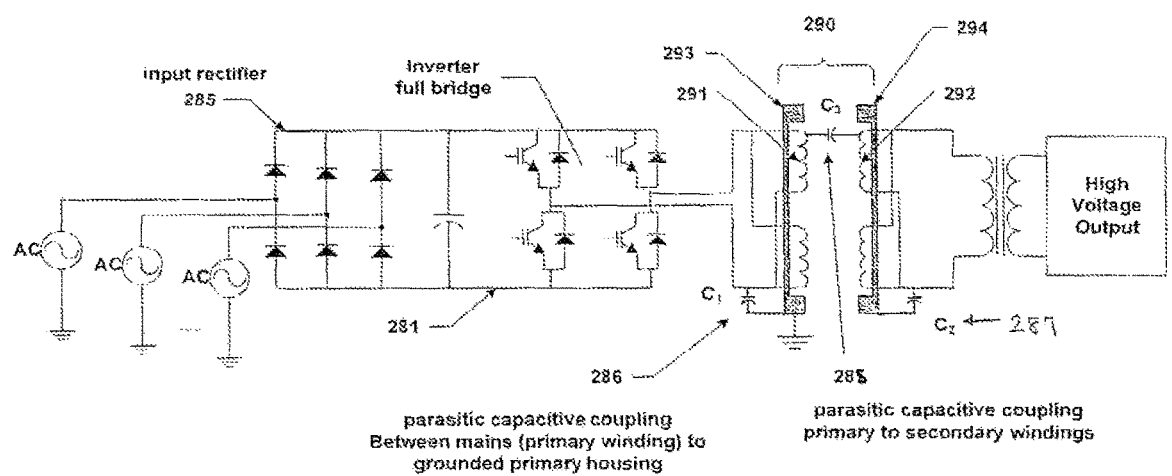
FIG. 2 shows a diagram of a connection of a non-isolated inverter to the primary winding of the rotary transformer.

FIG. 2 shows a diagram of a connection of a conventional inverter 281 to the primary winding of a rotary transformer 290, in a design in which the primary winding of the rotary transformer 290 is not isolated from the mains input. As shown in FIG. 2, the rotary transformer 290 includes a primary winding 291, a secondary winding 292, a primary housing 293 for the primary winding 291, and a secondary housing 294 for the secondary winding 292. In the diagram illustrated in FIG. 2, a mains input rectifier 285 feeds a high frequency inverter 281 that drives the primary winding 291 in the rotary transformer housing 293, providing a source of current flow referenced to earth through parasitic capacitances 286 (C1), 287 (C2), and 288 (C3) in the rotary transformer 290. The capacitance between the primary winding 291 and housing 293 (which is referenced to the grounded chassis frame) provides a path for the current i, which is given by:

$$i = 2 \cdot \pi \cdot V \cdot f C \quad (1)$$

In equation (1) above:
V=the applied voltage or in the case of a full bridge inverter the buss voltage minus loss;
f=operating frequency of the inverter; and
C=the capacitance between the winding and the frame or housing.

The above-described coupling action to the secondary winding 192 also provides a current source to charge the rotating structure and requires a high current galvanic path to ground for a single fault condition on the secondary side, defeating the value and concept of "non-contact" power transfer.

Figure 3:
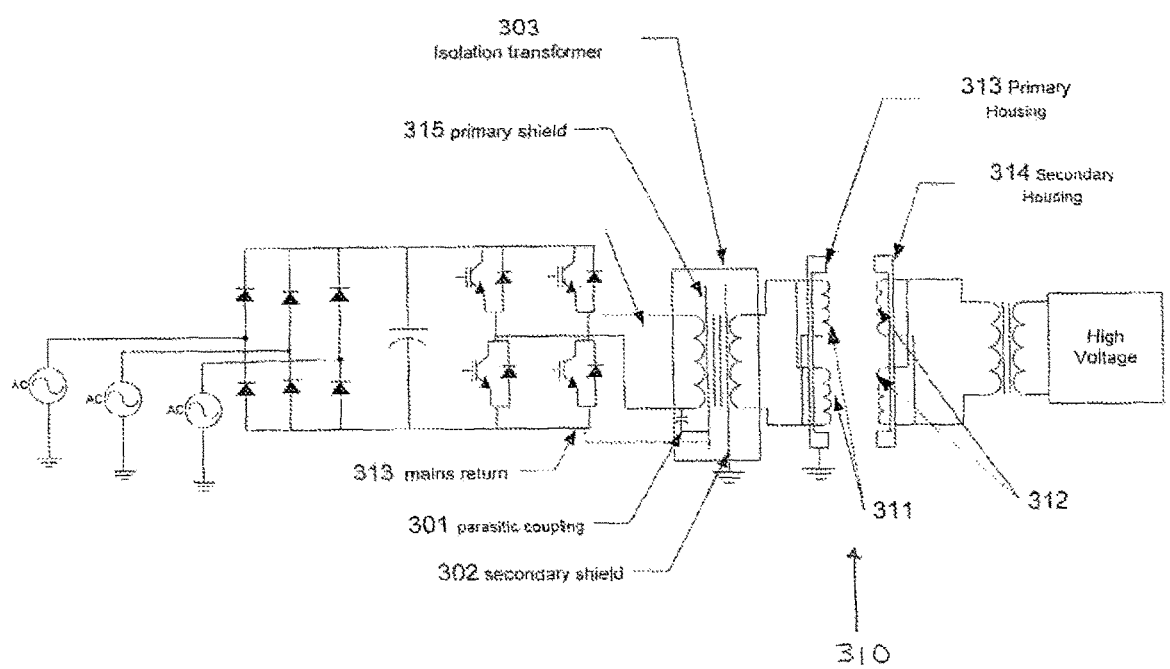
FIG. 3 provides a more detailed illustration of an isolation transformer that operates between the inverter output and the primary of a rotational power transformer.

Referring to FIG. 3, a more detailed illustration is provided for the isolation transformer 303, which is shown as operating between the inverter output and a primary winding of a power rotary transformer 310.

As seen in FIG. 3, the rotary transformer 310 includes a primary winding 311, a primary housing 313 for the primary winding 311, a secondary winding 312, and a secondary housing 314 for the secondary winding 312.

As shown in FIG. 3, a primary shield 315 is provided between the main power input to the primary winding 311 of the rotary transformer 310. The shield 315 provides a return path for the primary parasitic capacitance 301 to return to the main power input, through a mains return path 313. A secondary shield 302 shown in FIG. 3 on the secondary winding of the isolation transformer 303 to ground removes the 360 Hz component present on the primary shield 315 from being coupled to the secondary winding of the transformer 303 by returning it to the inverter's PE ground point.

The high frequency isolation transformer 303 effectively eliminates all leakage currents and provides for a safe condition in situations that include but are not limited to: failure of the insulation between the primary housing 313 and the primary winding 311; primary/secondary windings 311/312 insulation failure; or human contact with the primary housing 313 and/or the secondary housing 314.

Figure 4:
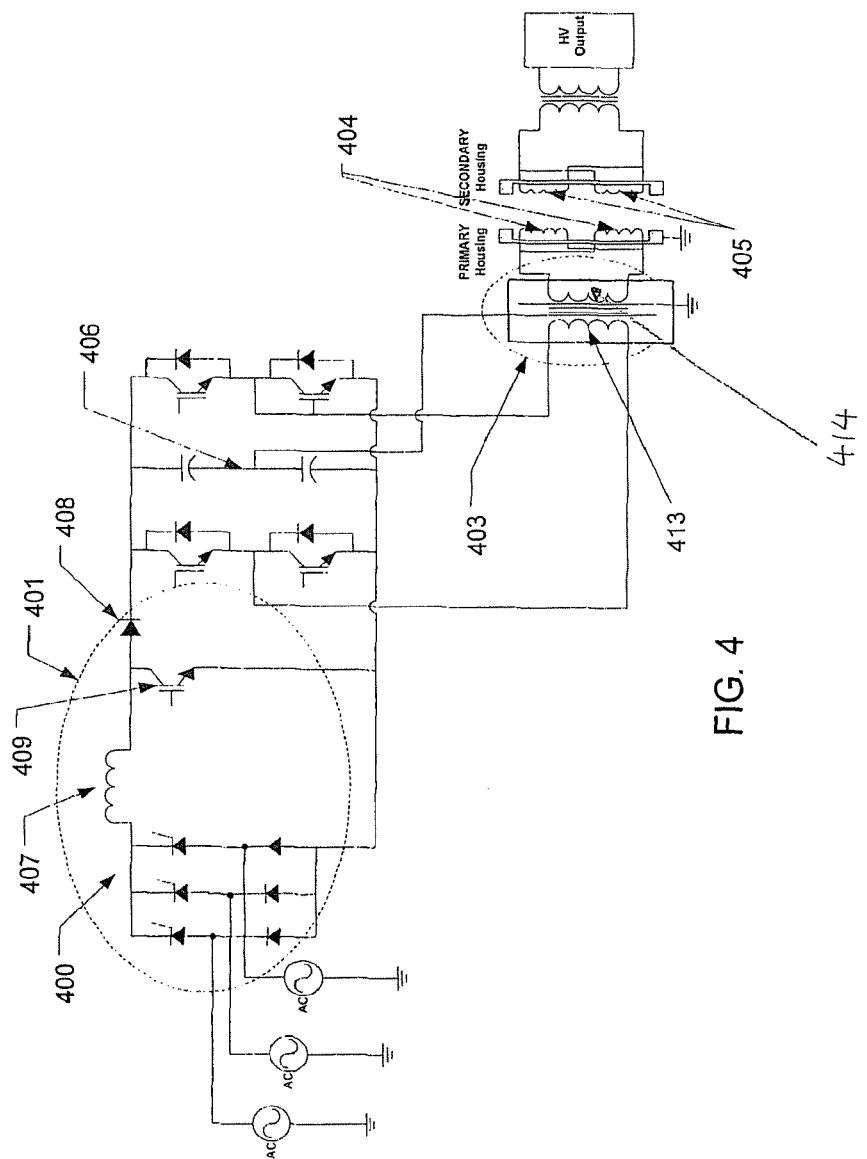
FIG. 4 illustrates a distributed AC/AC module that includes a boost pre-regulator and that is coupled to a bridge inverter and an isolation transformer.

FIG. 4 illustrates a distributed AC/AC that is coupled to an isolation transformer 403, unlike the non-isolated configuration shown in FIG. 2. The isolation transformer 403 has a primary winding 413 and a secondary winding 414. Also shown are the primary winding 404 and secondary winding 405 of the gapped rotary transformer.

FIG. 4 illustrates a shield connection that is to either one leg of the rectified input of the main power supply, or to a center potential, as illustrated through reference numeral 406 in FIG. 4. When the shield connection is to such a low frequency point (e.g., about 360 Hz), the leakage current is provided a return path to reduce the transferred energy (leakage) to and/or from the secondary winding 414 of the isolation transformer 403.

As shown in FIG. 4, the isolation transformer 403 allows for multiple windings on the primary of the transformer, where the multiple windings can connect to desired ones of a plurality of inverters. In this way, the collective outputs of the inverters can be summed to a single output, rather than the inverters being galvanically connected directly.

An embodiment of the boost inverter stage is shown in FIG. 4. The boost stage 401 consists of an input rectifier 400, boost inductor 407, boost switch 409, and boost diode 408. The output voltage of the boost stage is controlled via PWM of the boost switch. Alternate configurations in which inductor location is relocated to the AC side of the mains rectifier can be implemented.

Series resonant inverters that turn off the switching elements prior to completion of the resonant half cycle are operating above resonance and hence are referred to as "above resonant inverters". The turn off of a switch directs the current to be conducted through the anti-parallel diode of a complimentary switch allowing it to turn on under zero voltage. Turn off under current requires a fast switch/diode to reduce the turn off losses, a feature of FETs (Field-Effect Transistors). At higher power levels, the on resistance of the FET results is significant and limits power handling capabilities. Recent improvements in IGBT (Insulated Gate Bipolar Transistor) technology has allowed IGBTs to be used successfully at lower voltages (<1200V) and currents (<100). However, IGBTs in large power devices (1200V@600 A) have limited availability of the type required for very high power (>100 kW) that can also operate at switching frequencies over 50 kHz with low losses.

Above resonant inverters provide power regulation by moving away from resonance to a higher frequency that provides changes to the resonant impedance as defined by the Q of the circuit. Practical limitations in stability and the speed of high voltage rectifiers significantly limit the dynamic range of the output power for a series resonant system.

An alternative mode of operation for a series resonant circuit is below resonance. In such a system the switches turn off after the half cycle completes while the resonant energy circulates through an anti-parallel diode of the switch, allowing the device to turn off under zero current. Below resonant inverters have limitations at minimum power, because they are difficult to operate in a discontinuous manner without introducing significant ripple in the regulated output.

In accordance with one embodiment of the present disclosure, a variable frequency/phase inverter operates from near resonance to above resonance utilizing the reflected capacitance in the load circuitry presented in parallel to the transformer inductances of the power circuit (non-series resonant). The advantage is a reduction in circulating currents at above resonant operation (lower power), offering a well behaved power stage that can cease operation mid inverter cycle (for arc control), provide a wide range of output power and eliminate the need for high current/voltage capacitor elements in series with the main power transmission.

Figure 5:
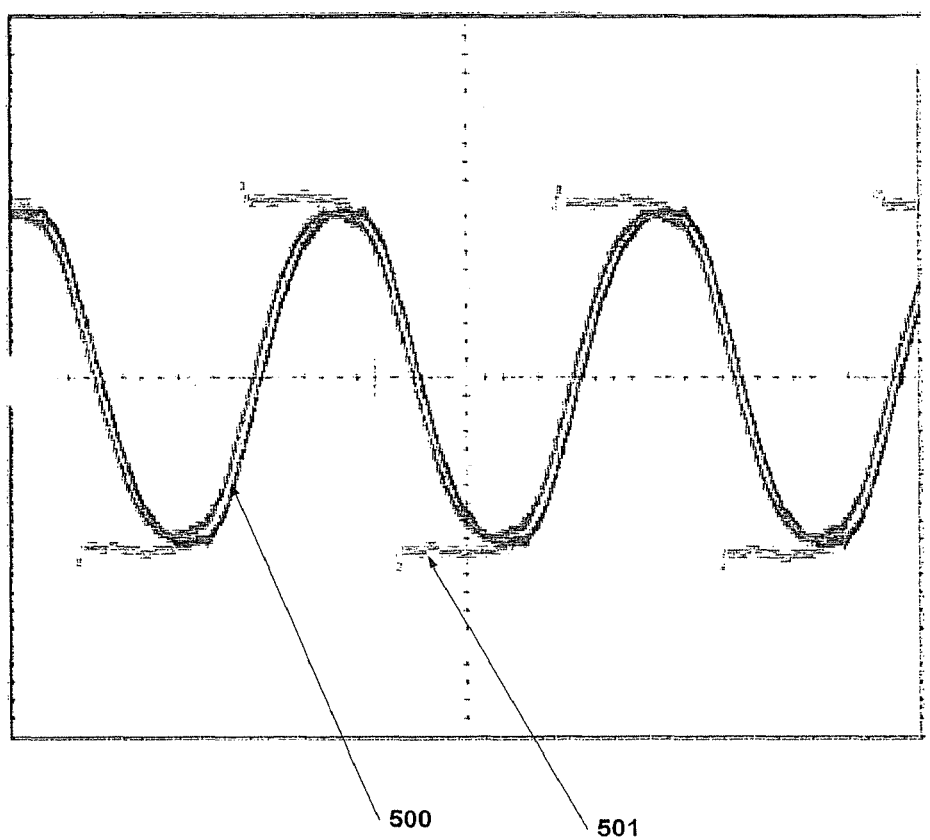
FIG. 5 illustrates high power, lower frequency resonant current waveforms without phase shifting.

FIG. 5 illustrates high power, lower frequency resonant current waveform(s) 500 without phase shifting of the inverter voltage source 501. As illustrated in FIG. 5, maximum power is derived while at resonance, and continuously decreases as the frequency is increased.

To further extend the dynamic range of the power transfer system described in the present disclosure, phase control of the multi-phase windings may be utilized, in one embodiment of the present disclosure. The high voltage secondary winding may exhibit a parasitic capacitance, in conjunction with that of the high voltage output stages reflected to the primary side. They reduce, and may even eliminate, the need for a capacitive element to be added.

Figure 6:
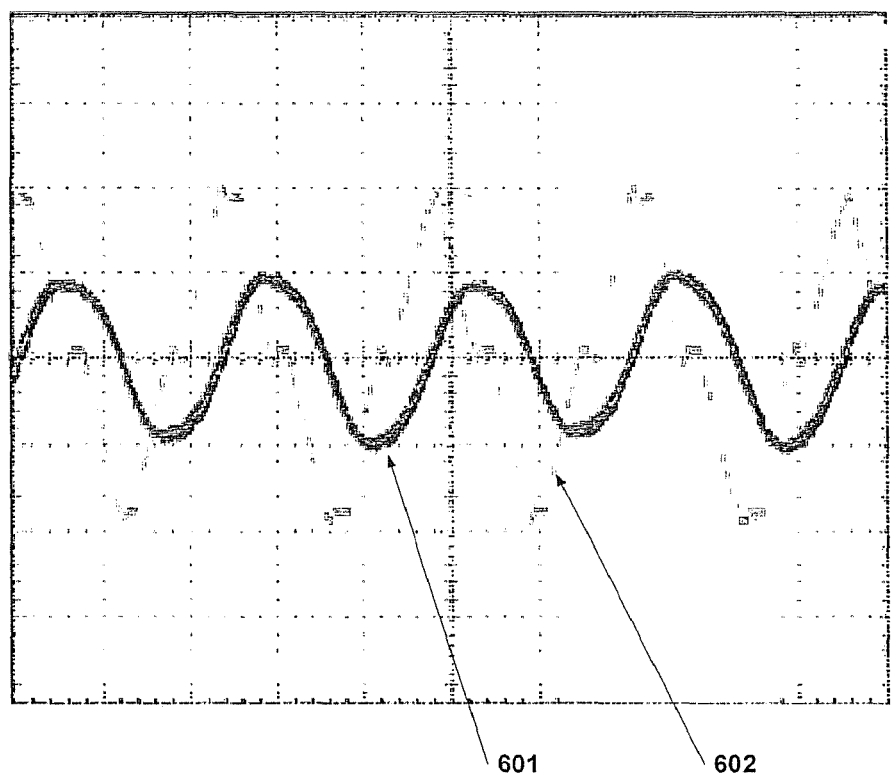
FIG. 6 illustrates phase shifting at higher frequency, which achieves low power.

FIG. 6 illustrates resonant current waveforms 601 with phase shifting present at the inverter drive voltage 602. As illustrated in FIG. 6, the currents are reduced. At approximately 2.5 times the resonant frequency the phasing of the multiphase inverters at the primary of the isolation transformer are altered, thereby further reducing the transferred power. In this manner zero output power can be achieved while limiting the upper operating frequency. Additionally, the phase shifted waveforms are preferably canceled and/or combined at the inverter stage or the primary side of the isolation transformer, as opposed to being canceled in the primary of the HV transformer, thereby preventing the creation of large circulating currents in the transformer windings. These circulating currents create heat, reduce efficiency, and limit duty cycle of the power transfer system.

Figure 7:
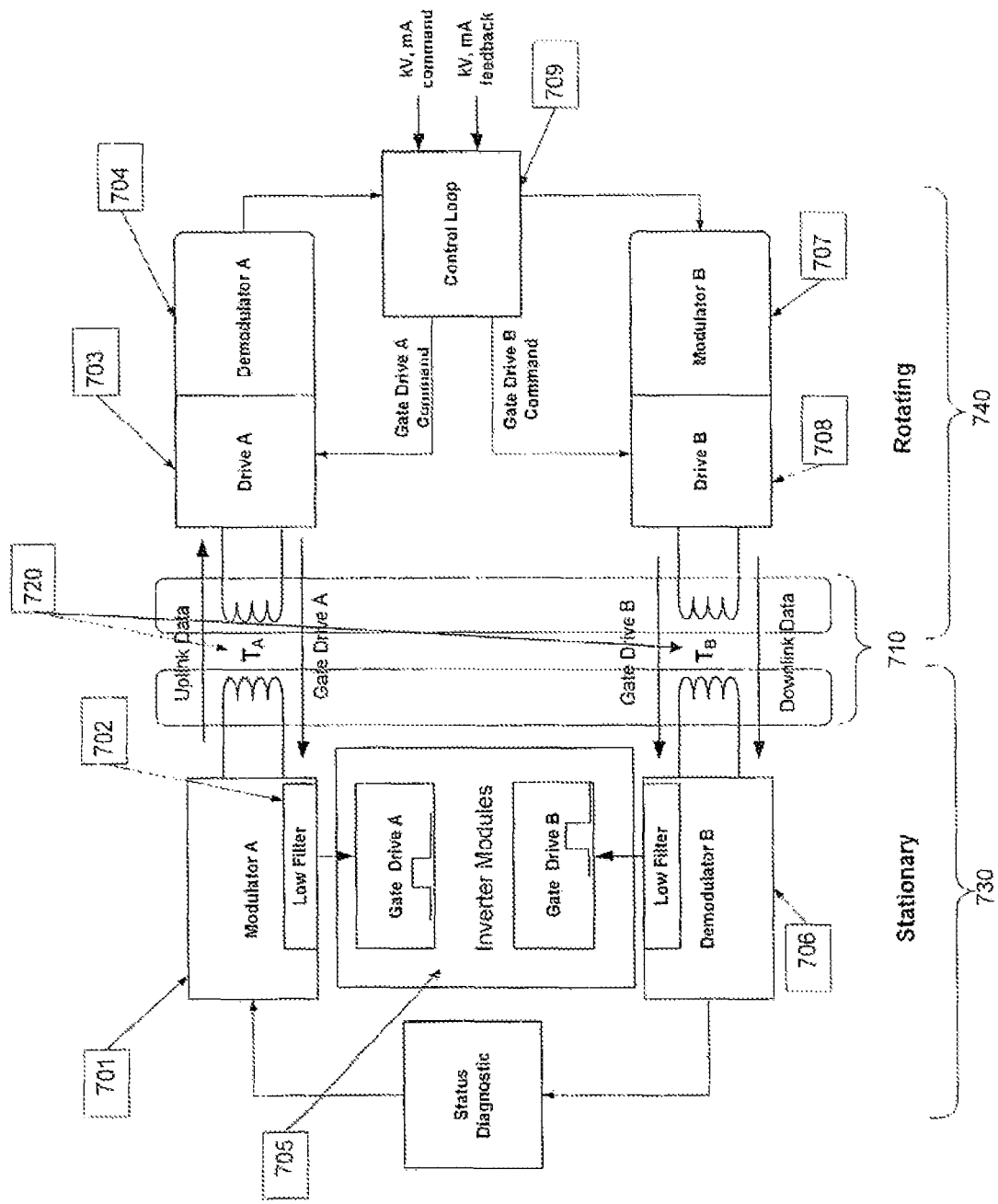
FIG. 7 illustrates non-contact control of delivered power with direct gate drive and bi-directional supervisor communication.

FIG. 7 illustrates non-contact control of delivered power with direct gate drive and bi-directional supervisor communication. As in previous figures, FIG. 7 illustrates a rotary transformer 710 that is configured to transfer induced power between a stationary side 730 and a rotating side 740. In the embodiment illustrated in FIG. 7, the critical real time gate drive signal timing is generated by a control loop circuit 709, and is presented to drive circuits 703, 708 which utilize rotary transformer windings 720 ($T_A$), ($T_B$) as part of the gate drive transformers. They have a 1:1 ratio in the illustrated embodiment. Different ratios may be used in different embodiments. In this technique the timing of both gating signals is preserved in the analog signal for pulse width and relative phase. While two timing channels, 720 ($T_A$),($T_B$), are shown in FIG. 7, the number of timing channels is not limited to two, and any other number of timing channels may be included in other embodiments of the present disclosure.

In the illustrated embodiment, a bi-directional communication channel between the stationary and rotating elements is accomplished by super positioning a very high frequency signal on the timing waveforms of 720. Data is sent to the rotating side 740 by using modulator 701 and extracting the data via a demodulator 704. The very high frequency signal riding on the gate drive signal is removed via a filter 702 and presented directly to the gate drive circuitry of a plurality of inverter modules 705. This process is likewise used to send data to the stationary side 730 using modulator 707 and demodulator 706.

The demodulated signal is then processed to provide non-real time control functions, including but not limited to diagnostics, status and interlocks features.

In the illustrated embodiment, the real-time gate drive control signals and non real-time data are sent via coupled windings contained within the rotary transformer elements 720 ($T_A$, $T_B$). It should be appreciated that control of the power delivery system is not limited to the above-described technique, and that transfer mechanisms may be used for the same purpose, in different embodiments of the present disclosure.

Figure 8:
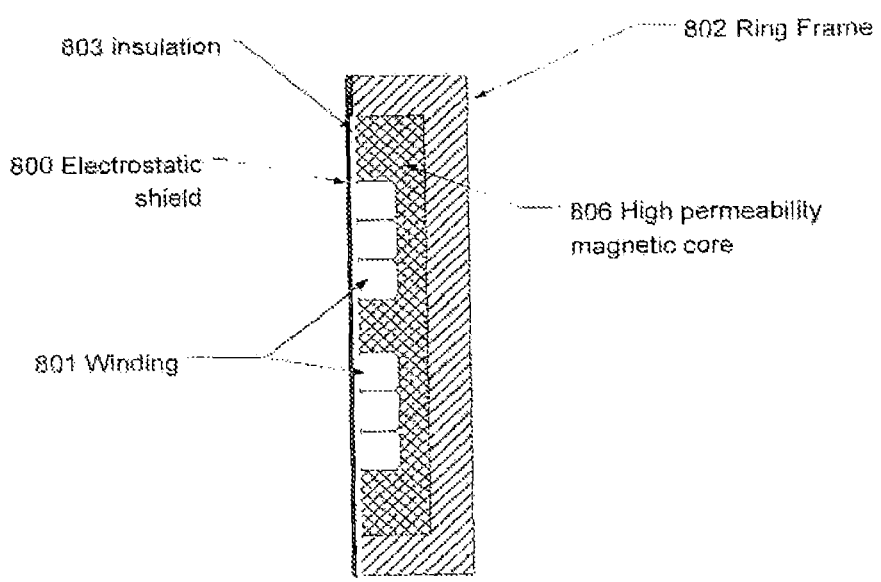
FIG. 8 illustrates an electrostatic shield that shields the windings of the rotating transformer.

FIG. 8 illustrates an electrostatic shield 800 that shields the windings 801 of the rotary transformer. The e-field of the primary and secondary windings of a transformer produce radiated emissions. The nature of a rotary transformer requires a gap that prevents the winding from being shielded by the housing. As seen in the embodiment illustrated in FIG. 8, a non-overlapping foil shield 800 is provided on an exposed surface of the winding 801. The shield is made of, and/or includes, a conducting foil and an insulating material 803. Examples of the insulating material 803 include, but are not limited to, a 2 millimeter layer of Kapton to prevent a "shorted turn". The foil is comprised of an appropriate material to minimize eddy currents. Different types of insulating material 803 may be included in different embodiments of the present disclosure. A high permeability magnetic core 806 may surround the winding 801. One side of the shield 800 is connected to the rotary transformer (or ring) frame 802 or to an alternative return path, when using the above-described isolation method, further reducing radiated noise.

Electrostatic Discharge

The various aspects of the power transfer system design described in this disclosure provide for an effective solution to high speed, no maintenance rotary power transfer. Although a non-contact arrangement for power transfer is a desirable feature to eliminate brush wear from existing designs, a need for a low force, non-power, non-signal related galvanic connection may arise. Without a galvanic path (such as an air bearing configuration) there can be a static charge build up on the rotating element due to friction with the air.

Figure 9:
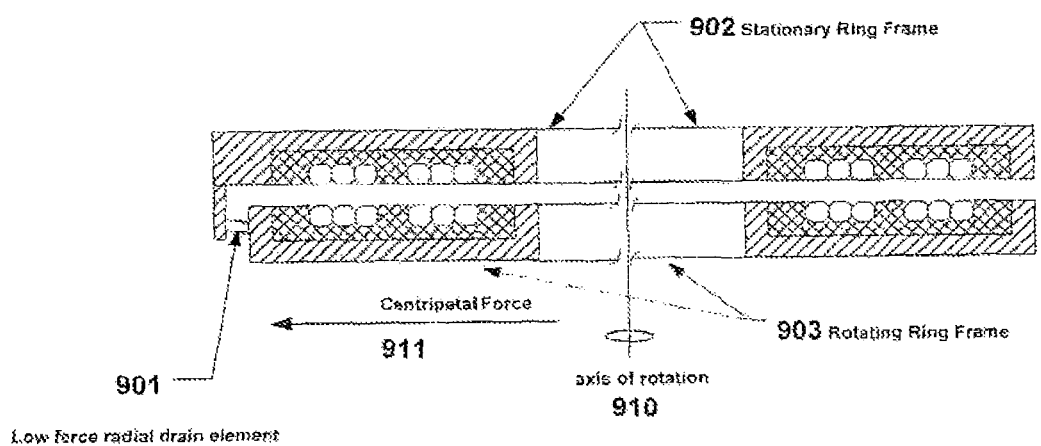
FIG. 9 illustrates a low force galvanic connection that prevents static charge build up on the rotating element due to friction with the air.

FIG. 9 illustrates a low force galvanic connection, or other type of electrostatic discharger, that prevents static charge build up on the rotating coupling element due to friction with the air. In FIG. 9, a stationary ring frame 902 and a rotating ring frame 903 are shown, where the rotating ring frame 903 is rotatable about the stationary ring frame 902 around an axis of rotation 910. A simple low force connection, such as a connection 901 shown in FIG. 9, provides such a galvanic path, or other type of electrostatic discharger. The orientation of the drain element(s) is such that the centripetal force 911, due to the rotation about the axis 910, provides the required contact force. An additional feature of the design is to increase bearing life in a CT system of the type using traditional bearing, by eliminating micro-discharges through the bearing and race which can otherwise reduce the life time of the bearing.

It should be appreciated that discharge path or "drain wire" of the power delivery system is not limited to a galvanic connection or the above-described technique, and that different transfer mechanisms may be used for the same purpose, in different embodiments of the present disclosure. As just one example, in one embodiment the electrostatic discharger may be an ionic connection, rather than a galvanic connection. In this embodiment, an ionic source may be employed in order to neutralize charge build up.

Figure 10:
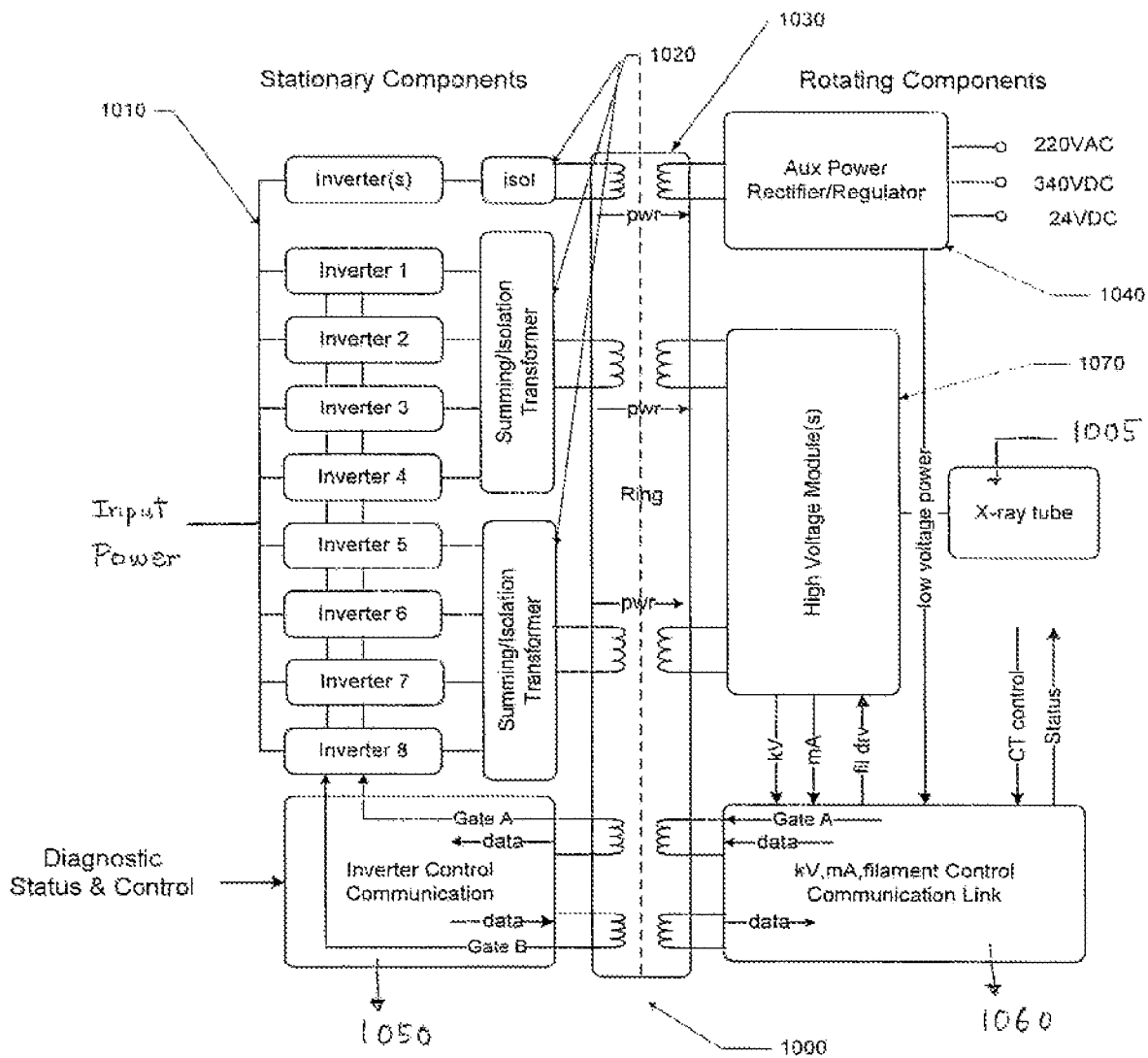
FIG. 10 illustrates a system level diagram of the non-contact power transfer system illustrated in FIG. 1.

FIG. 10 illustrates a system level diagram of a non-contact power transfer system 1000, also shown in FIG. 1. The non-contact power transfer system 1000 includes a plurality of modular inverters 1010 with pre-regulators of the type described in conjunction with FIG. 4. The outputs of these modular inverters 1010 (three shown as an example) are summed by multiple shielded isolation transformers 1020 of the type shown and described in conjunction with FIG. 1. These isolation transformers 1020 are configured to drive a rotary transformer 1030.

A regulator 1040 isolates and regulates various auxiliary outputs. The secondary windings of the rotary transformer 1030 associated with the main inverter module 1010 are connected to high voltage module(s) 1070. The non-contact power transfer system 1000 includes the electrostatic shield and discharge element described above, with integrated real time gate drive and bi-directional communication.

In the illustrated embodiment, the non-contact power transfer system 1000 is configured to deliver power to an x-ray tube 1005. A kV, mA, and filament control communication link 1060 is shown. In the illustrated embodiment, in which the power transfer system 1000 is shown as being used for a CT system, the control communication link 1060 communicates with CT control unit(s) in a CT system, for example receiving CT control information and generating status information. The link 1060 also communicates with the high voltage modules 1070, and is connected to the secondary windings of the rotary transformer 1030. An inverter control communication unit 1050 is also shown. This unit receives diagnostic status and control information, and communicates the received information to the inverters 1010.

FIG. 11 illustrates a system level diagram of a CT system 1100 that utilizes the non-contact power delivery system 100 illustrated in FIG. 1. As explained in conjunction with FIGS. 1 and 10, the power delivery system 100 transfers power between a stationary side 1170 and a rotational side 1171. An isolation transformer 1140 is located on the stationary side 1170.

In a conventional CT system, a source of x-rays (typically an x-ray tube) and x-ray detector array(s) are typically mounted on a rotating gantry. In the CT system 1100 illustrated in FIG. 11, an x-ray tube 1105 and a data acquisition system 1110 are disposed on the rotational side 1171. The data acquisition system 1110 acquires and processes x-ray data, which are generated when the x-rays from the x-ray tube 1105 are detected by x-ray detector array(s) in the data acquisition system, after the x-rays have traversed through a target object. The x-ray data are transmitted by a transmitter 1120 to a CT image reconstruction unit 1130 disposed on the stationary side 1170, via a receiver 1125. The CT image reconstruction unit 1130 uses image processing and reconstruction algorithms, which may include but are not limited to interpolation and backprojection, to reconstruct a tomographic image of the target object using the x-ray data transmitted from the rotational side 1171 to the stationary side.

The CT system 1100 illustrated in FIG. 11 represents only one example of systems in which the non-contact power delivery system described above can be used. The non-contact power delivery system may be used in any application that requires transfer of power between a stationary side and a rotational side. A number of features disclosed in the present disclosure may be useful in power delivery systems, and are summarized below.

A device is described that isolates one or more outputs of a power inverter system from a primary winding of a rotary transformer. The rotary transformer adapted to couple power between at least one stationary element and at least one rotational element. The power inverter system is configured to provide input power to the primary winding of the rotary transformer. The device includes an isolation transformer configured to receive a sum of the one or more outputs of the power inverter system and to drive the primary winding of the rotary transformer.

A control system is described that controlling delivery of power by a rotary transformer that has a primary winding and a secondary winding and that is configured to transfer power between stationary coupling elements disposed on a stationary side and rotational coupling elements disposed on a rotating side. The control system includes one or more control elements disposed on the rotating side. The control elements are configured to provide timing signals to the stationary side in order to control one or more power inverter stages that provide input power to the primary winding of the rotary transformer.

The control elements including at least one control loop circuit that is disposed on the rotating side and that is configured to control delivery of power from the secondary winding of the rotary transformer. The control loop circuit is configured to close a feedback loop on desired and actual performance of one or more output power converters. The output power converters receive transmitted power from the rotary transformer, and convert the received power to a desired range for the rotational coupling elements.

The control system may further include gate drive windings that are coupled to the control loop circuit, and are configured to transmit real time gate drive waveforms from at least some of the rotational coupling elements to at least some of the power inverter stages.

An electrostatic discharger is described for a non-contact power delivery system that transfers power between one or more stationary coupling elements, and one or more rotational coupling elements configured to rotate with respect to the stationary coupling elements. The electrostatic discharger is configured to substantially prevent static discharge from accumulating on one or more of the rotational coupling elements.

In one embodiment, the electrostatic discharger may be a galvanic connection between the rotational coupling elements and the stationary coupling elements.

A rotary transformer is described that is used in a power delivery system. The rotary transformer transfers power between stationary coupling elements on a stationary side of the transformer and rotational coupling elements on a rotational side of the transformer. The rotary transformer includes a primary winding and a secondary winding. The windings of the rotary transformer are configured for dual use that allows for bi-directional communication through one or more coupled high-frequency modulated signals. Such a dual use may comprise a first use in which power signals or timing signals are transmitted through the windings, and a second use that provides for bi-directional communication between the stationary side and the rotational side.

In summary, an isolated multichannel, contactless, modular rotary power transfer system has been disclosed that includes a split rotary transformer that couples one or more stationary elements with one or more rotational elements. An isolation and summing transformer drives the primary of the rotary transformer in a multi phase configuration, and sums the stationary power elements in a dynamic manner to respond to load conditions. The secondary winding of the rotary transformer drives selected rotational elements to produce a desired range of regulated power. The rotational based control that provides variable frequency and phase control of the power stages and multiple windings of the rotational element(s) eliminate high bandwidth digitized data transfer to the stationary side, providing a wide dynamic range of output power, high efficiency, and fast rise times.

While certain embodiments have been described of a power transfer system, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A control system for controlling a power inverter disposed on a stationary side of an imaging system and configured to deliver power to a radiation source and one or more other elements disposed on a rotating side of the imaging system, the control system comprising:
   a control element disposed on the rotating side and coupled to a high voltage output module for supplying power at a first voltage to the radiation source and an auxiliary output regulator for supplying power at a second voltage lower than the first voltage to the one or more other elements, wherein the control element is configured to receive information from the high voltage output module and the auxiliary output regulator and generate a first analog timing signal for controlling the power inverter;
   a modulator configured to combine the first analog timing signal with a second signal to yield a modulated signal;
   a first rotary transformer configured to transmit the modulated signal from the rotating side to the stationary side and comprising:
      a first gate drive winding disposed on the rotating side and coupled to the control element; and
      a second gate drive winding disposed on the stationary side; and
   gate drive circuitry disposed on the stationary side and coupled between the second gate drive winding and one or more gate terminals of one or more transistors of the power inverter, wherein the gate drive circuitry comprises a demodulator configured to receive the modulated signal, separate the first analog timing signal from the second signal, and apply the first analog timing signal directly to the one or more gate terminals.

2. The control system of claim 1, wherein the control element is configured to compare a desired operating parameter of the radiation source to an actual operating parameter of the radiation source and to modify the first analog timing signal based upon a difference between the desired operating parameter and the actual operating parameter.

3. The control system of claim 2, wherein at least one of:
   the desired operating parameter corresponds to a desired voltage to be applied to the radiation source and the actual operating parameter corresponds to an actual voltage applied to the radiation source; or
   the desired operating parameter corresponds to a desired current to be supplied to the radiation source and the actual operating parameter corresponds to an actual current supplied to the radiation source.

4. The control system of claim 1, comprising a supervisory circuit configured to receive the second signal from the demodulator.

5. The control system of claim 1, wherein the gate drive circuitry is configured to send, via the first rotary transformer, a first communication signal to the control element.

6. The control system of claim 5, wherein the first communication signal describes a desired operating parameter of the radiation source.

7. The control system of claim 6, wherein the control element is configured to compare the desired operating parameter to an actual operating parameter of the radiation source and to modify the first analog timing signal based upon a difference between the desired operating parameter and the actual operating parameter.

8. The control system of claim 1, wherein the power is delivered from the stationary side to the rotating side via a second rotary transformer different than the first rotary transformer.

9. The control system of claim 1, wherein:
   the control element is configured to generate a second timing signal, different than the first analog timing signal, for controlling the power inverter, and
   the control system comprises a second rotary transformer, different than the first rotary transformer, configured to transmit the second timing signal from the rotating side to the stationary side for application to the power inverter.

10. The control system of claim 1, wherein:
    the control element is configured to generate a second timing signal for controlling a second power inverter disposed on the stationary side,
    the control system comprises a second rotary transformer comprises:
       a third gate drive winding disposed on the rotating side and coupled to the control element; and a fourth gate drive winding disposed on the stationary side and coupled to the second power inverter, the first gate drive winding and second gate drive winding operate in tandem to deliver the first analog timing signal between the control element and the power inverter, and the third gate drive winding and fourth gate drive winding operate in tandem to deliver the second timing signal between the control element and the second power inverter.

11. The control system of claim 10, wherein:
the gate drive circuitry is configured to send, via the first gate drive winding and the second gate drive winding, a first communication signal to the control element.

12. The control system of claim 10, wherein:
the power inverter comprises a high voltage power inverter for generating first power to be supplied to the high voltage output module, and
the second power inverter comprises an auxiliary power inverter for generating second power to be supplied to the auxiliary output regulator.

13. The control system of claim 1, wherein a pulse width of the first analog timing signal is preserved between the control element and the one or more gate terminals of the power inverter.

14. The control system of claim 1, wherein the control element is configured to generate a filament drive signal that is supplied to the high voltage output module for driving the radiation source.

15. A control system for controlling a power inverter disposed on a stationary side of a computed tomography (CT) system and configured to deliver power to a plurality of element disposed on a rotating side of the CT system, the control system comprising:
a control element disposed on the rotating side and coupled to an auxiliary output regulator for generating a first voltage output applied to a first element of the plurality of elements and generating a second voltage output different than the first voltage output and applied to a second element of the plurality of elements, wherein the control element is configured to:
determine a desired pulse width of signals output from the power inverter and generate a timing signal have the desired pulse width based upon at least one of a voltage or current command and at least one of a voltage or current feedback from at least one of the first element or the second element, and
manage the first voltage output and the second voltage output;
a modulator configured to combine the timing signal with a second signal to yield a modulated signal;
a rotary transformer configured to transmit the modulated signal from the rotating side to the stationary side and comprising:
a first gate drive winding disposed on the rotating side and coupled to the control element; and
a second gate drive winding disposed on the stationary side; and
gate drive circuitry disposed on the stationary side and coupled between the second gate drive winding and one or more gate terminals of one or more transistors of the power inverter, wherein the gate drive circuitry comprises a demodulator configured to receive the modulated signal, separate the timing signal from the second signal, and apply the timing signal to the one or more gate terminals.

16. The control system of claim 15, wherein:
the gate drive circuitry is configured to send, via the rotary transformer, a first communication signal to the control element, and
the first communication signal describes a desired operating parameter of the first element.

17. The control system of claim 16, wherein:
the control element is configured to determine a desired pulse timing of phase, and
the timing signal is based upon the desired pulse timing of phase.

18. A control system for controlling a power inverter disposed on a stationary side of a computed tomography (CT) system and configured to deliver power to a radiation source disposed on a rotating side of the CT system, the control system comprising:
a control element disposed on the rotating side and coupled to a high voltage module configured to supply power to the radiation source, wherein the control element is configured to generate an analog timing signal for controlling the power inverter, configured to generate a first communication signal, and configured to generate a filament drive signal for driving the radiation source;
a modulator configured to combine the analog timing signal with the first communication signal to yield a modulated signal;
a rotary transformer configured to transmit the modulated signal from the rotating side to the stationary side and comprising:
a first gate drive winding disposed on the rotating side and coupled to the control element; and
a second gate drive winding disposed on the stationary side and coupled to the power inverter; and
gate drive circuitry disposed on the stationary side and coupled between the second gate drive winding and one or more gate terminals of one or more transistors of the power inverter, wherein the gate drive circuitry comprises a demodulator configured to receive the modulated signal, separate the analog timing signal from the first communication signal, and apply the analog timing signal to the one or more gate terminals, wherein the analog timing signal remains in an analog domain from a time at which the analog timing signal is generated at the control element until a time at which the analog timing signal is applied to the one or more gate terminals.

19. The control system of claim 18, the analog timing signal is maintained in the analog domain without digitization or coding between the time at which the analog timing signal is generated at the control element until the time at which the analog timing signal is applied to the one or more gate terminals.

20. The control system of claim 18, wherein a pulse width of the analog timing signal is preserved between the control element and the one or more gate terminals of the power inverter.

* * * * *